United States Patent [19]

Doyle

[11] Plant 4,094

[45] Aug. 23, 1977

[54] DOYLE'S BLACKBERRY

[76] Inventor: Thomas E. Doyle, 1600 Bedford Road, Washington, Ind. 47501

[21] Appl. No.: 741,115

[22] Filed: Nov. 11, 1976

[51] Int. Cl.[2] ..... A01H 5/03

[52] U.S. Cl. ..... Plt./46

[58] Field of Search ..... Plt./46

*Primary Examiner*—Robert E. Bagwill

*Attorney, Agent, or Firm*—Burns, Doane, Swecker & Mathis

[57] ABSTRACT

The invention relates to a new and distinct variety of Blackberry plant most nearly resembling the Wild Blackberry which exhibits (1) an absence of thorns or prickles, (2) the common occurrence of palmately compound leaves having five leaflets, (3) sturdy canes which support an unusually large upright-arching plant, (4) unusually long trailing stems, and (5) substantially round berries which form in an unusually abundant quantity and ripen over an unusually extended period.

4 Drawing Figures

SUMMARY OF THE INVENTION

My invention concerns a new and distinct variety of Blackberry plant which was discovered by me during 1970 growing in my berry patch at 1600 Bedford Road, Washington, Indiana. Growing in the same berry patch where the new variety was discovered were many Wild Blackberries, Tame Blackberries, Youngberries, Everbearing Raspberries, Boysenberries and Grapes. The new variety likely resulted from open pollination and is of unknown parentage. The new variety is believed to most nearly resemble the Wild Blackberry.

The highly desirable characteristics of the new plant rendered it readily discernible from the other berry plants growing in the area, and it was preserved.

My discovery differs from the Wild Blackberry by, inter alia, the following combination of characteristics:

1. an absence of thorns or prickles,
2. the common occurrence of palmately compound leaves having five leaflets,
3. sturdy canes which support an unusually large upright-arching plant,
4. unusually long trailing stems,
5. substantially round berries which form in an unusually abundant quantity and ripen over an unusually extended period.

Observations of the new variety have been made at Washington, Ind., where it has satisfactorily withstood winter temperatures as low as −5° F.

Asexual reproduction of my discovery by cuttings has been performed by me at Washington, Ind. This propagation shows that the unique combination of characteristics comes true to form and is established and transmitted through succeeding propagation.

BRIEF DESCRIPTION OF THE DRAWINGS

The accompanying drawings show typical specimens of the new variety in color as nearly true as is reasonably possible to make the same in a color illustration of this character.

DETAILED DESCRIPTION OF THE DISCLOSURE

The following description was made from plants growing at Washington, Ind. Color terminology employed is to be accorded its ordinary dictionary significance.

Figure 1:
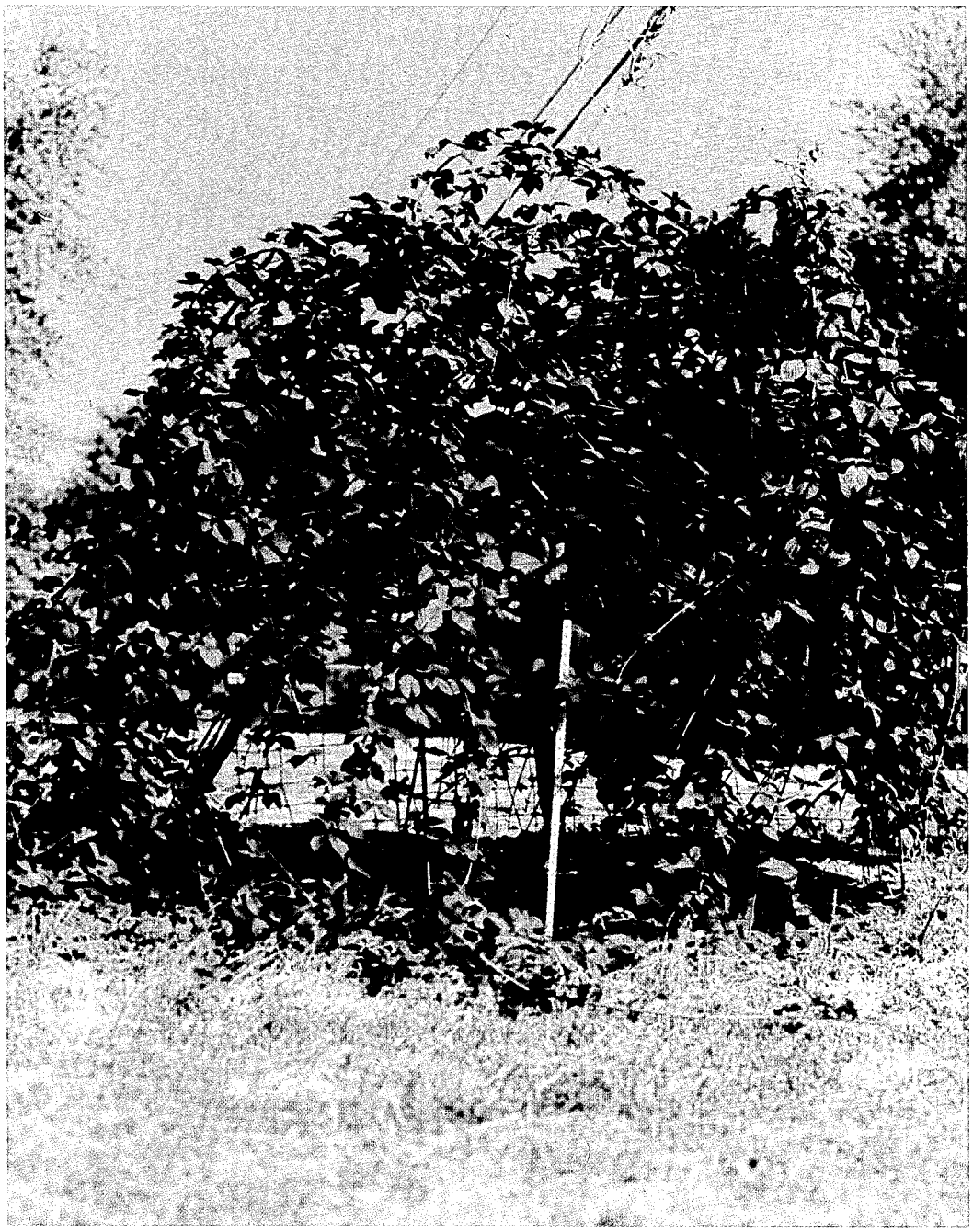
FIG. 1 shows a typical four year old plant of the new variety. A yard stick is vertically positioned in the photo to illustrate the unusually large size of the plant.
Figure 2:
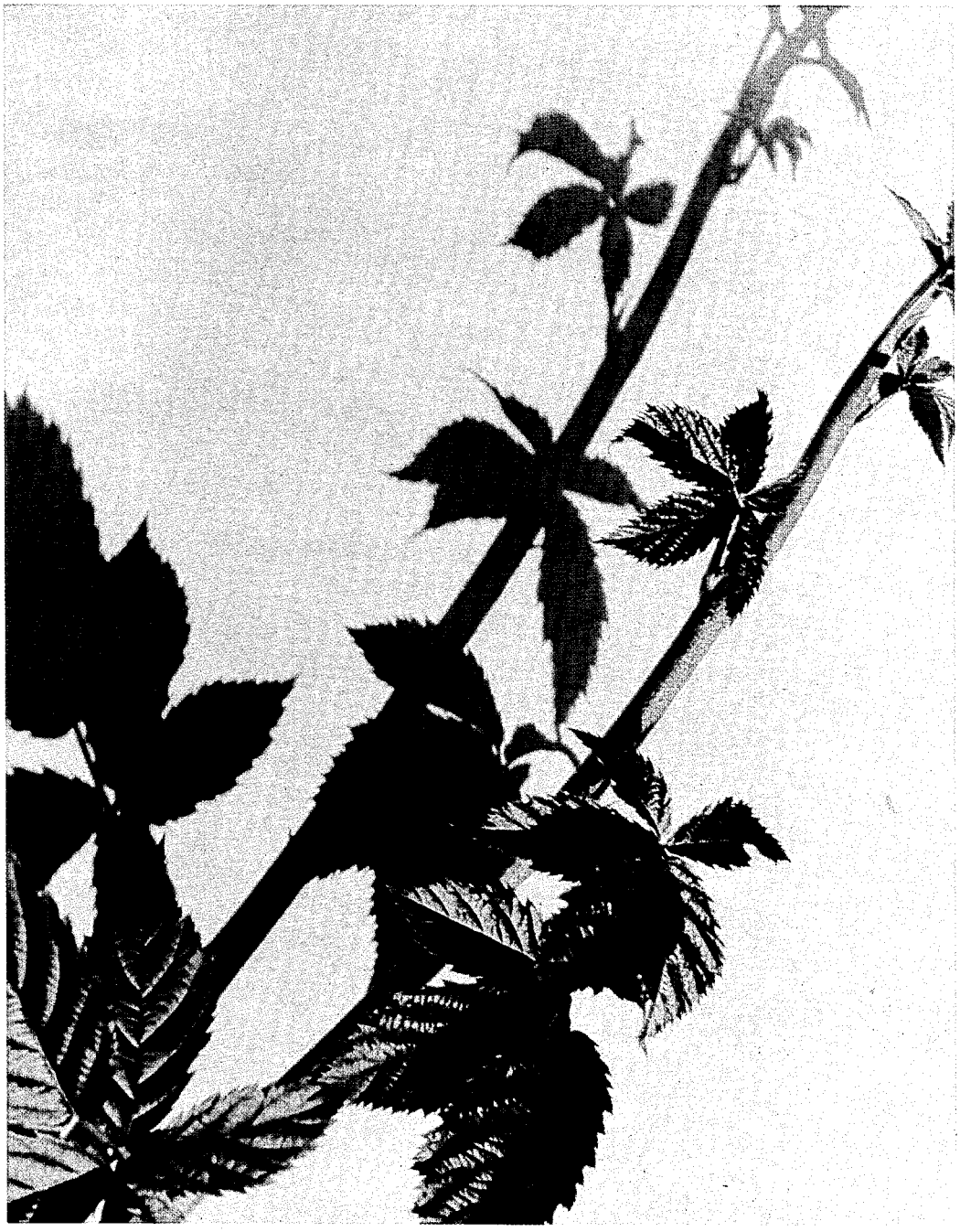
FIG. 2 shows a portion of a newly formed thornless stem of the new variety bearing newly formed palmately compound leaves having five leaflets.
Figure 3:
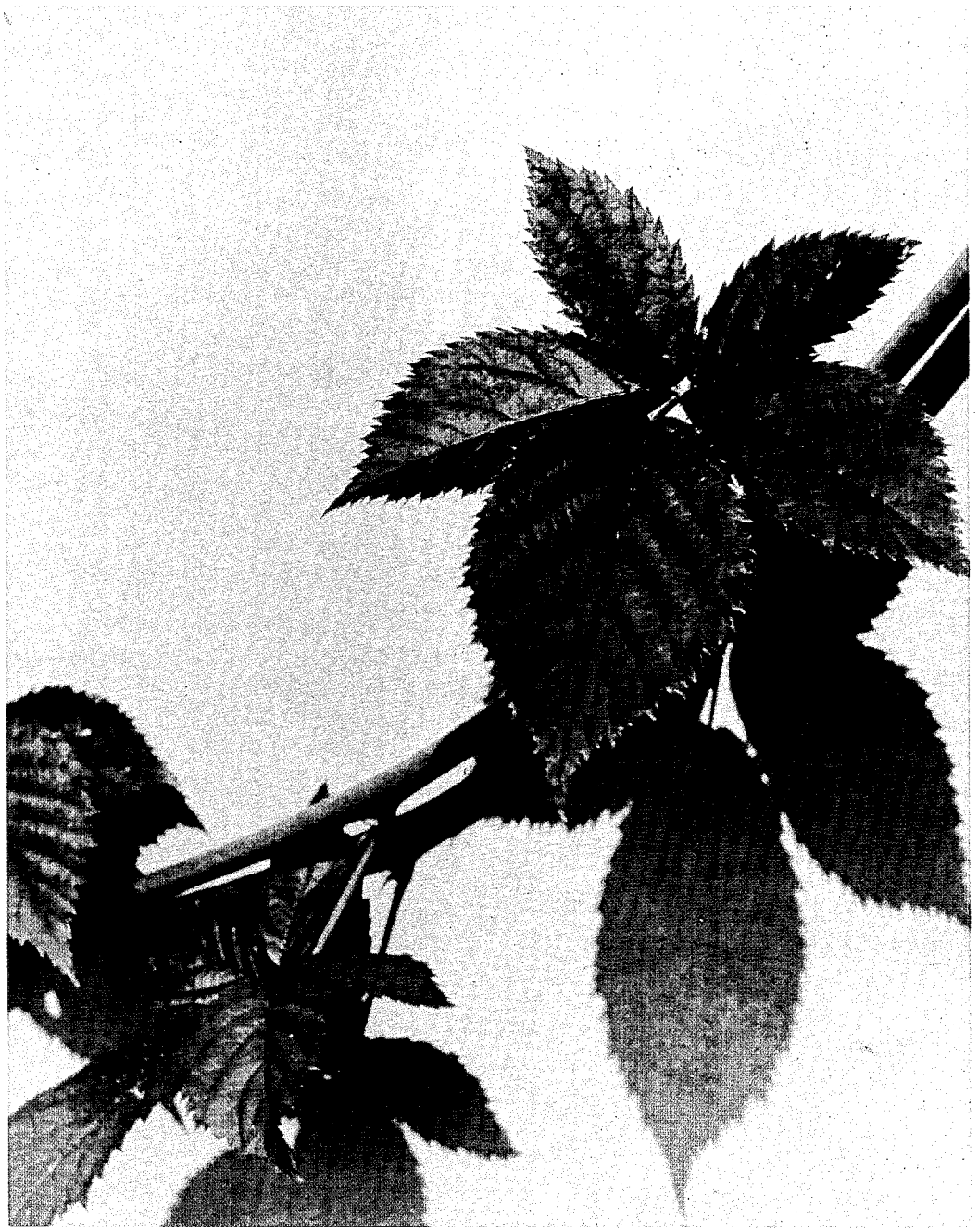
FIG. 3 shows a portion of a thornless stem of the new variety bearing more mature palmately compound leaves having five leaflets.

Plant Form: Large size; narrow based; vigorous; upright-arching shrub; unusually long trailing stems or branches; deciduous. The plant as illustrated in FIG. 1 may achieve a height of seven feet or more, a width of 10 feet or more at its widest point, and exhibit trailing stems of 25 to 30 feet or more in length.

Environment: The variety does well in either the full sun or in the shade.

Canes: Sturdy; biennial; often 1 to 1½ inches in diameter when mature; commonly one to four canes per plant; light green in color with occasional vertical maroon streaks; much branched, arching downwards with the tips of the stems often trailing on the ground. There is little tendency for the plant to send up suckers.

Thorns and Prickles: Totally absent on any part of plant, none have been observed.

Foliage: Trifoliate or palmately compound with four and commonly five leaflets. The terminal leaflet is always the largest. The leaflets tend to be dark green in color similar to that of the Wild Blackberry. The underside of the leaflets is paler in color than the upper surfaces, both surfaces having scattered hirsute hairs. The stems tend to be russet in color, and the roots white in color. The petioles tend to be 1 to 1½ inches long. The petiolules are quite short. The leaflets are obovate in shape, the margins being irregularly serrated with occasional rough lobes.

Flowers: Profuse and extended appearing in mid-April to mid-May.

Figure 4:
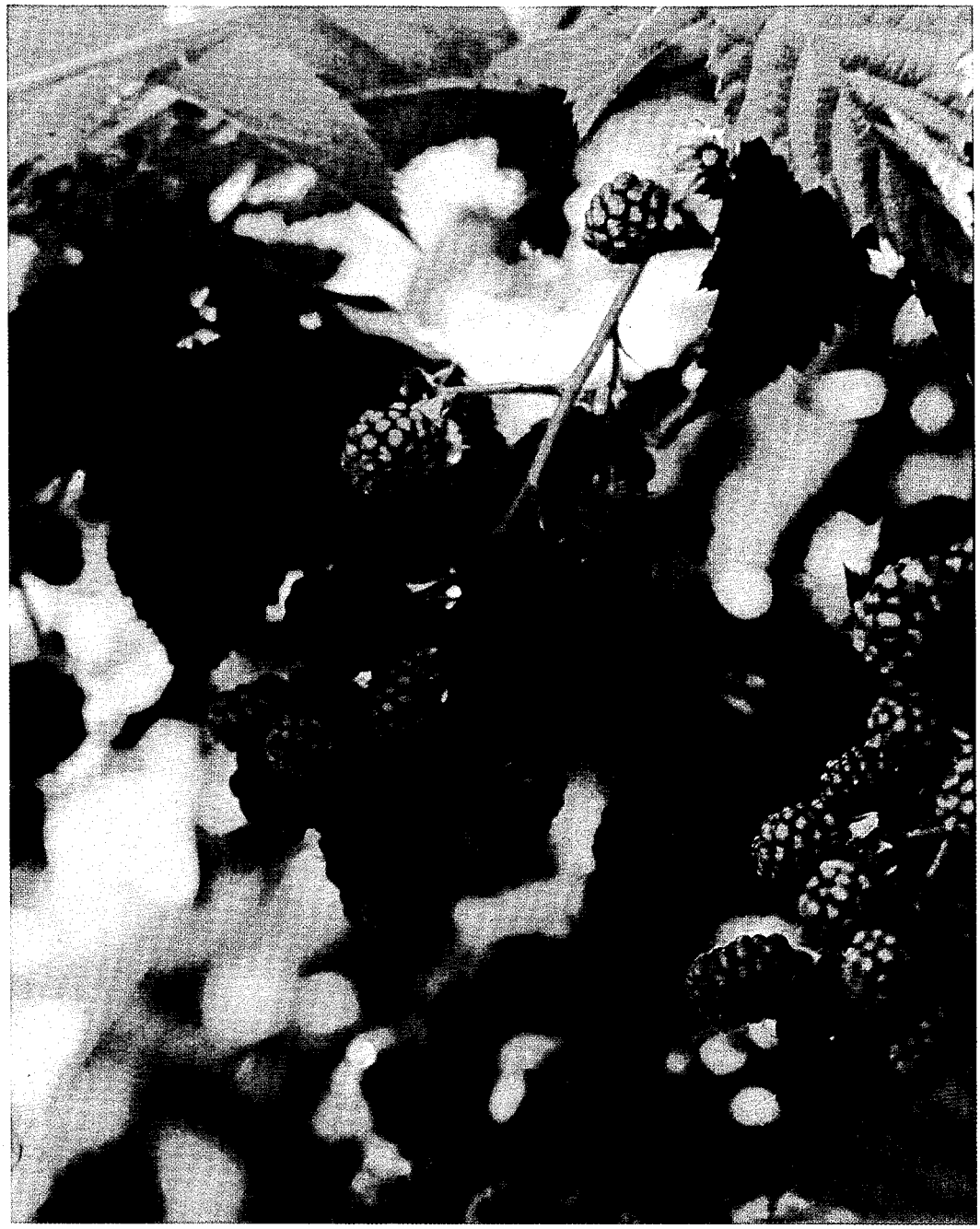
FIG. 4 shows clusters of the substantially round berries of the new variety which exhibit various stages of ripeness.

Fruit: Substantially round berries born on widely branched terminal clusters usually of approximately 20 to 100 berries on lateral shoots appearing under each leaf having a distinctive Blackberry taste similar to that of Wild Blackberries. The fruit is generally ¾ to 1⅛ inches in length. The ripened berries have a fluorescent blue-black appearance as illustrated in FIG. 4, and ripen over an unusually extended period of time (e.g. approximately 60 days). The plant as illustrated in FIG. 1 produces an abundant harvest of berries totaling 10 to 20 gallons. The ripened fruit is retained well upon the plant and stays firm for several days following picking even without refrigeration. The berry shape is similar to that of the Wild Blackberry.

Disease: The variety has not contracted rusts, leaf spot, cane blight or other common Blackberry plant diseases and appears to be resistant.

The new variety herein described is being named Doyle's Blackberry.

Having thus described and illustrated my new variety of Blackberry plant what is claimed as new and desired to be secured by Letters Patent is set forth in the following claim:

1. A new and distinct variety of Blackberry plant most nearly resembling the Wild Blackberry substantially as shown and described, characterized particularly as to novelty by the unique combination of (1) an absence of thorns or prickles, (2) the common occurrence of palmately compound leaves having five leaflets, (3) sturdy canes which support an unusually large upright-arching plant, (4) unusually long trailing stems, and (5) substantially round berries which form in an unusually abundant quantity and ripen over an unusually extended period.

* * * * *